United States Patent [19]

Ward

[11] 4,367,657

[45] Jan. 11, 1983

[54] SLUDGE SAMPLER

[75] Inventor: Ralph C. Ward, Los Alamos, N. Mex.

[73] Assignee: The United States of America as represented by the United States Department of Energy, Washington, D.C.

[21] Appl. No.: 277,435

[22] Filed: Jun. 25, 1981

[51] Int. Cl.³ .............................................. G01N 1/12
[52] U.S. Cl. ................................ 73/864.61; 73/864.65
[58] Field of Search ........... 73/864.51, 864.61, 864.63, 73/864.65, 864.66

[56] References Cited

U.S. PATENT DOCUMENTS

| | | | |
|---|---|---|---|
| 1,416,354 | 5/1922 | Johnson | 73/864.51 |
| 1,511,591 | 10/1924 | Colligan | 73/864.63 |
| 2,203,019 | 6/1940 | Johnson | 73/864.65 |
| 2,593,830 | 4/1952 | Baker | 73/864.65 |
| 2,634,612 | 4/1953 | Quist | 73/864.63 |
| 2,702,125 | 2/1955 | Willinger | 73/864.51 |

Primary Examiner—S. Clement Swisher
Attorney, Agent, or Firm—Robert W. Weig; Paul D. Gaetjens; Richard G. Besha

[57] ABSTRACT

The disclosure relates to a sludge sampler comprising an elongated generally cylindrical housing containing a baffle containing an aperture. Connected to the aperture is a flexible tubing having a valve for maintaining and releasing pressure in the lower end of the housing and exiting the upper end of the housing. The lower end of the housing contains a ball check valve maintained in closed position by pressure. When the lower end of the device contacts the sludge bed, the pressure valve is opened, enabling sludge to enter the lower end of the housing. After the sample is collected the valve is closed. An upsetting pin opens the valve to empty a sludge sample after the sample is removed from the fluid.

6 Claims, 2 Drawing Figures

SLUDGE SAMPLER

BACKGROUND OF THE INVENTION

The invention relates to sludge sampling and more particularly to an apparatus for obtaining samples of sludge at the bottom of a body of water or other fluid without diluting the samples by admission of water or fluid into the sampler. This invention is a result of a contract with the Department of Energy (Contract No. W-7405-ENG-36).

At present there is a need to monitor our environment in order to determine quantitatively as well as qualitatively what pollutants or objectionable materials are present as well as what desirable materials, such as bacteria, and the like are present. Apparatus in accordance with the present invention have utility in monitoring sludge in cesspools, stream beds, and downstream rivers from nuclear reactors to determine what, if any, leakage might be occurring of undesirable radioactive or other materials. Such materials end up in the sludge since they are usually heavy metals and the like. Those skilled in the art will appreciate that apparatus in accordance with the invention can be used to monitor sludge at the bottom of any body of water or other fluid.

SUMMARY OF THE INVENTION

One object of the present invention is to provide sludge samples without dilution by water or other fluids.

Another object of the present invention is to provide sludge samples from the bottom of bodies of water of varying depth.

In accordance with the present invention, there is provided a sludge sampler comprising an elongated generally cylindrical housing having an upper end and a lower end, a baffle containing an aperture disposed within the housing, and a flexible tube for pressure control communicating with the aperture in the baffle. The flexible tubing extends out the upper end of the housing. A ball check valve, an upsetting pin and an upsetting pin guide are disposed at the lower end of the housing. Pressure within the lower end of the housing between the baffle and the check valve excludes all but minimal fluid entry into the sampler until it enters the sludge bed. At this time, the valve opens and the sludge enters the sampler. When the desired amount of sludge is gathered or when the lower end is full of sludge, the device is withdrawn from the water or other fluid body. In a preferred embodiment, a plurality of removable sections are provided for the upper end to provide for a selection of housing length commensurate with the depth of fluid over the sludge bed.

One advantage of the present invention is that sludge may be obtained from the bottom of a body of fluid without contamination or dilution from the fluid.

Another advantage of the instant invention is that the sampler thereof is variable in length to accommodate sludge at the bottom of fluid bodies of varying depth.

Still another advantage of the invention is that it is simple to operate and economical to construct.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION OF A PREFERRED EMBODIMENT OF THE INVENTION

Figure 1:
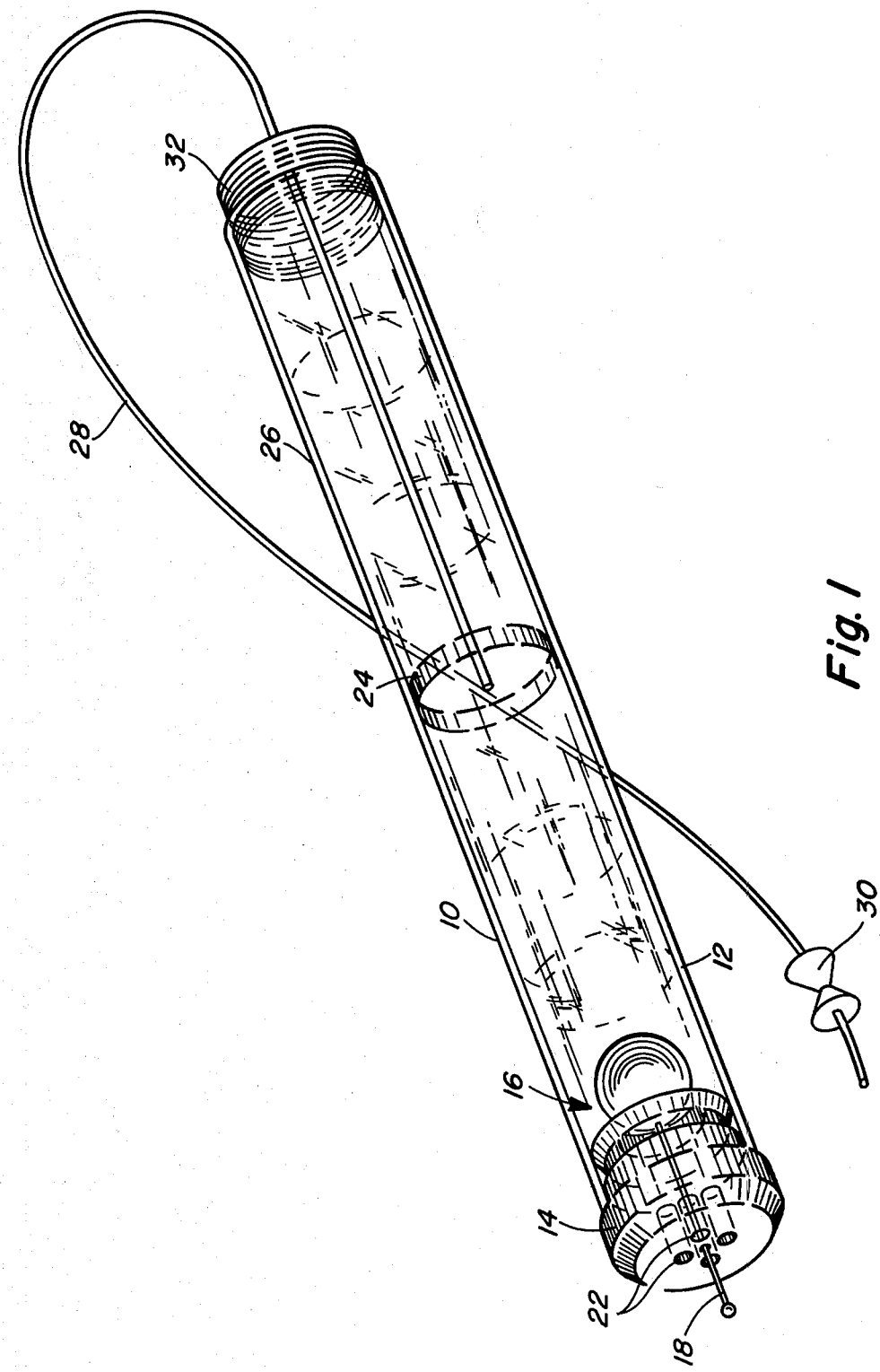
FIG. 1 illustrates a perspective showing of a preferred embodiment of the invention.
Figure 2:
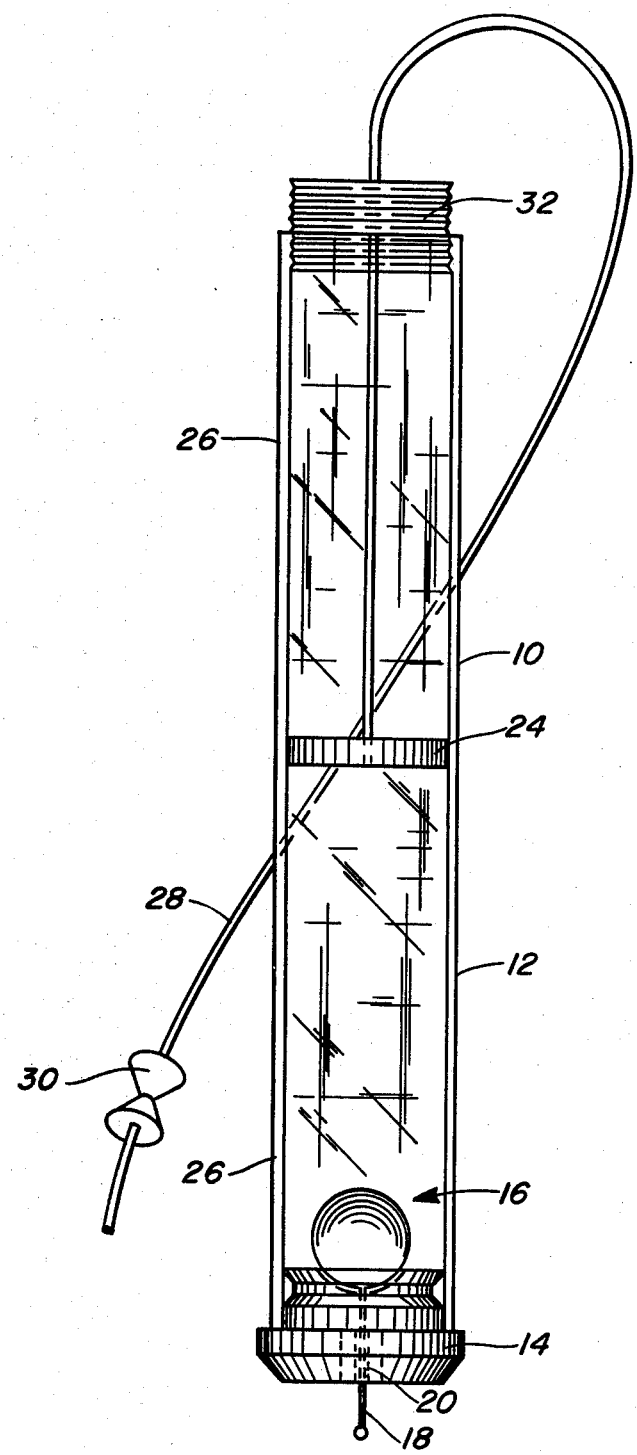
FIG. 2 is a side view of the preferred embodiment of the invention.

Reference is now made to FIGS. 1 and 2 which show a preferred embodiment of the invention comprising an elongated generally cylindrical housing 10 which may comprise for example a transparent acrylic tube, a glass tube, either transparent or translucent, or a transparent or translucent tube formed from other plastics and rigid materials. Too, a metal tube could be utilized. Those skilled in the art will appreciate that the housing could aslo be square, triangular, rectangular, pentagular, hexagular or other polyhedral shape in cross section. In the preferred embodiment, the housing has an outside diameter of 2 inches and an inside diameter of 1½ inches yielding a wall thickness of ¼ inch. The housing preferably comprises a plurality of sections which may be threadably or otherwise joined together in order to sample sludge at the bottoms of bodies of fluid having various depths. In the preferred embodiment the lower part of the housing 12 although it may be of any desired and suitable length is 6 inches long and incorporates a ball check valve 16 having an upsetting pin 18 seated in an end plate 14 disposed in the bottom end of the housing. An upsetting pin guide 20 is provided in end plate 14 to guide pin 18. A plurality of apertures 22 are provided in end plate 14 as pathways for sludge to enter lower portion 12 of housing 10. A baffle 24 which in the preferred embodiment comprises a 1½ inch in diameter disk having a quarter inch center drilled hole is cemented or otherwise affixed airtight in housing 10. Above disk 24 is upper end 26 of housing 10 which may comprise the one section shown or as before mentioned a plurality of joined sections of tubing. A flexible tube 28 is sealed to the quarter inch aperture drilled in baffle 24. Flexible tube 28 may comprise a PVC tube or other well-known flexible rubber or plastic type tube such as Neoprene ®, silicon and the like. A flexible tube 28 leads out of the housing and through any extensions thereon through a valve 30 installed at the end of the tube. Tube 28 maintains the pressure desired below disk 24 in lower end 12, thereby excluding all but minimal water entry into lower end 12 until the sludge bed is contacted. When bottom is encountered, valve 30 on tube 28 is opened to allow sludge to enter lower end 12 of the sampler. The ball check valve closes and retains the sample while the sampler is being withdrawn from the body of fluid. The sample is then transferred to a sample bottle by depressing the upsetting pin.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A sludge sampler comprising:
    an elongated generally cylindrical housing having an upper end and a lower end;
    a baffle containing an aperture disposed within said housing separating said upper and lower ends;
    a flexible tube having a valve for presure control within said housing communicating with said aperture in said baffle and exiting said housing at said upper end;
    a ball check valve, an upsetting pin and an upsetting pin guide disposed at said lower end of said housing.

2. The invention of claim 1 wherein said housing comprises a transparent acrylic.

3. The invention of claim 1 wherein said housing between said baffle and said upper end comprises a plurality of removable sections providing for selective housing length.

4. The invention of claim 3 wherein said sections are threadably connectable.

5. The invention of claim 1 wherein said housing is about one inch to about three inches in diameter.

6. The invention of claim 1 wherein said fexible tube has an inside diameter of from about one-eighth inch to about one-half inch.

* * * * *